(12) United States Patent
Letcher et al.

(10) Patent No.: US 6,858,440 B1
(45) Date of Patent: Feb. 22, 2005

(54) TAPERED TUBULAR OPTICAL WAVEGUIDE PROBE FOR MAGNETIC FOCUSING IMMUNOSENSORS

(75) Inventors: Stephen Letcher, Kingston, RI (US); He Cao, Breinigsville, PA (US); Hazem Baqaen, Cranston, RI (US); A. Garth Rand, Kingston, RI (US)

(73) Assignee: The Board of Governors for Higher Education, State of Rhode Island and Providence Plantations, Providence, RI (US)

( * ) Notice: Subject to any disclaimer, the term of this patent is extended or adjusted under 35 U.S.C. 154(b) by 110 days.

(21) Appl. No.: 10/285,954

(22) Filed: Nov. 1, 2002

Related U.S. Application Data

(60) Division of application No. 09/859,685, filed on May 17, 2001, now Pat. No. 6,645,777, and a continuation-in-part of application No. 09/435,081, filed on Nov. 5, 1999, now Pat. No. 6,254,830.
(60) Provisional application No. 60/204,337, filed on May 17, 2000.

(51) Int. Cl.[7] .................................. G01N 33/553
(52) U.S. Cl. .................. 436/518; 436/526; 436/73; 436/74; 436/533; 436/86; 436/63; 436/85; 436/164; 436/501; 436/534; 436/546; 435/7.1; 435/7.5; 435/7.93; 435/7.94; 435/7.95; 435/287.1; 435/287.2; 435/288.7; 435/281; 435/290.1; 422/82.07; 422/58; 422/68.1; 422/82.05; 422/50; 422/52; 422/82.08

(58) Field of Search .................. 436/518, 526, 436/73, 74, 533, 86, 63, 85, 164, 501, 534, 546; 435/7.1, 7.5, 7.93, 7.94, 7.95, 287.1, 287.2, 288.7, 281, 290.1; 422/82.07, 58, 68.1, 82.05, 50, 52, 82.08

(56) References Cited

U.S. PATENT DOCUMENTS

| 5,606,170 A | 2/1997 | Saaski et al. ............... 250/458 |
| 5,862,273 A | 1/1999 | Pelletier ...................... 385/12 |
| 6,254,830 B1 | 7/2001 | Pivarnik et al. ............. 422/82 |

OTHER PUBLICATIONS

Pivarnik et al. "Magnetic Focusing Immunosensor for the Datection of Salmonella typhimurium in Foods" SPIE, 3544, 41–49 (Jan. 1999).

Primary Examiner—Christopher L. Chin
Assistant Examiner—Pensee T. Do
(74) Attorney, Agent, or Firm—Gauthier & Connors LLP

(57) ABSTRACT

A waveguide probe for the detection of pathogens in a sample which comprises a laser, a first and a second tubes that converge at a point to form a proximal end. A magnet is positioned in the end to configure to focus paramagnetic microspheres attached to antigen/antibody/optically labeled antibody complexes in the field of view. The proximal end is polished to form an aperture.

8 Claims, 18 Drawing Sheets

TAPERED TUBULAR OPTICAL WAVEGUIDE PROBE FOR MAGNETIC FOCUSING IMMUNOSENSORS

CROSS-REFERENCE TO RELATED APPLICATIONS

This application claims the benefit of U.S. Provisional Application No. 60/204,337, filed on May 17, 2000 and is a continuation-in-part of U.S. application Ser. No. 09/435,081, filed Nov. 5, 1999. Now U.S. Pat. No. 6,254,830, which is a division of application Ser. No. 09/859,685, filed May 17, 2001, now U.S. Pat. No. 6,645,777.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of contract No. 97-35014480 awarded by the USDA, contract No. 97-352014480 awarded by the USDA/NRICGP and by grant No. DMI-9810541 by the NSF/STTR.

BACKGROUND OF THE INVENTION

1. Field of the Invention

An optical waveguide probe for assaying an analyte of interest.

2. Description of the Related Art

Fiber optic biosensors utilizing evanescent wave detection have been developed and used to detect drugs, toxins, and bacteria in food, clinical and environmental samples. The fibers were designed to use evanescent wave technology by immobilizing antibodies directly to the tip. The subsequent immunochemical reaction would bind the target antigens or organisms directly to the optical fiber and detection would occur within the evanescent wave. By utilizing the evanescent region, background from the fluorescently labeled detection antibodies was reduced to a minimum and did not interfere with detection. However, one limitation of the immunochemical assays is the regeneration of the antibodies. The antibody-antigen binding is not readily reversible and the conditions required to release the antigen result in the denaturation of the antibodies with subsequent loss of signal. Procedures have been developed for the reuse of the tapered fiber tips, but there exists a limit to the life of the sensing fiber. Disposable plastic tips have been developed to address this problem.

A second approach to the development of a reusable optical fiber biosensor utilized polystyrene microspheres for capture and isolation of the target organisms. Organisms bound to the polystyrene spheres and labeled with a fluorescently tagged secondary antibody can be detected by focusing the spheres ultrasonically into the evanescent region of a tapered fiber. The spheres used to capture the organisms could then be released and discarded leaving the sensing fiber ready for another reading. The use of a disposable to capture the target cells is very convenient and provides for the easy disposal of pathogen contaminated samples.

The parent application of the instant application, U.S. application Ser. No. 09/435,081, discloses a fiber optic magnetic-focusing immunosensor that is used to measure and detect pathogens in a sample. Paramagnetic microspheres labeled with surface-immobilized antibodies to a pathogen are mixed with the target pathogens and a fluorescent-labeled secondary antibody, for efficient one-step capture and fluorescent labeling of the cells. The microsphere-pathogen-fluorescent-label complex is placed in a cuvette in front of the fiber optic magnetic-focusing immunosensor. The fiber optic magnetic-focusing immunosensor, which is comprised of a magnetic tip, a collecting fiber and an excitation fiber, attracts the microspheres to a small concentrated spot on the side of the cuvette in front of the excitation and collecting fibers wherein the fluorescent signal is detected and measured.

The present invention comprises an improved magnetic-focusing immunosensor for detecting and measuring a pathogen in a sample.

BRIEF SUMMARY OF THE INVENTION

Broadly the invention comprises magnetic focusing of paramagnetic microspheres with a waveguide probe. Microspheres with immobilized antibodies interact throughout the analyte containing the target antigens, which, in turn, capture fluorescent-labeled antibodies in a standard sandwich assay. The bound antigen/antibody/fluorescent antibody complexes are magnetically attracted to the waveguide probe which contains the sensing volume of the excitation and collection fibers, while the uncaptured labeled fluorescent antibodies remain in bulk solution thereby reducing background fluorescence.

The invention comprises a hollow waveguide probe comprising first and a second tubes each having a middle portion and converging at a proximal end and a distal end. At the proximal end, the tubes converge to zero degrees. A magnet is positioned in the proximal end. An excitation fiber is in communication with the middle portion of the first tube which function as a transmission conduit. Excitation light is injected into the first tube and is guided to the proximal end where it illuminates the inner wall of a cuvette where fluorescent complexes are attracted by the magnet. The associated fluorescent signal is collected by the second tube and is guided to the distal end of the probe wherein the signal is detected and measured.

In a preferred embodiment of the invention a primary antibody specific for the antigen (pathogen) to be detected is coated on a magnetic bead and a secondary antibody is conjugated to a marker. A food sample is prepared and added to the medium. If the expected pathogen, such as *Salmonella typhimurium* is present, the pathogen binds to both antibodies forming a magnetic complex. The magnetic complex is attracted to the proximal end of the probe. The proximal end is polished to form a glass receiving aperture having a diameter which is approximately 2× the wall thickness of the first tube. The fluorescent signal received from the second tube is dettected. The signal can be detected by a fiber optic spectrometer in communication with a computer or a PIN detector in communication with an optical power meter.

In another aspect of the invention, a sample from the blood of mammals, fish or fowl is prepared and added to a medium comprised of primary antibodies specific for the anitgens (pathogens) to be detected whereby the primary antibodies are coated on a magnetic bead and a secondary antibody conjugated to a marker. The waveguide probe of the present invention could then be utilized as described above.

In yet another aspect of the invention, the waveguide probe is a portable unit that can be used for field testing.

BRIEF DESCRIPTION OF THE DRAWING(S)

Figure 12:
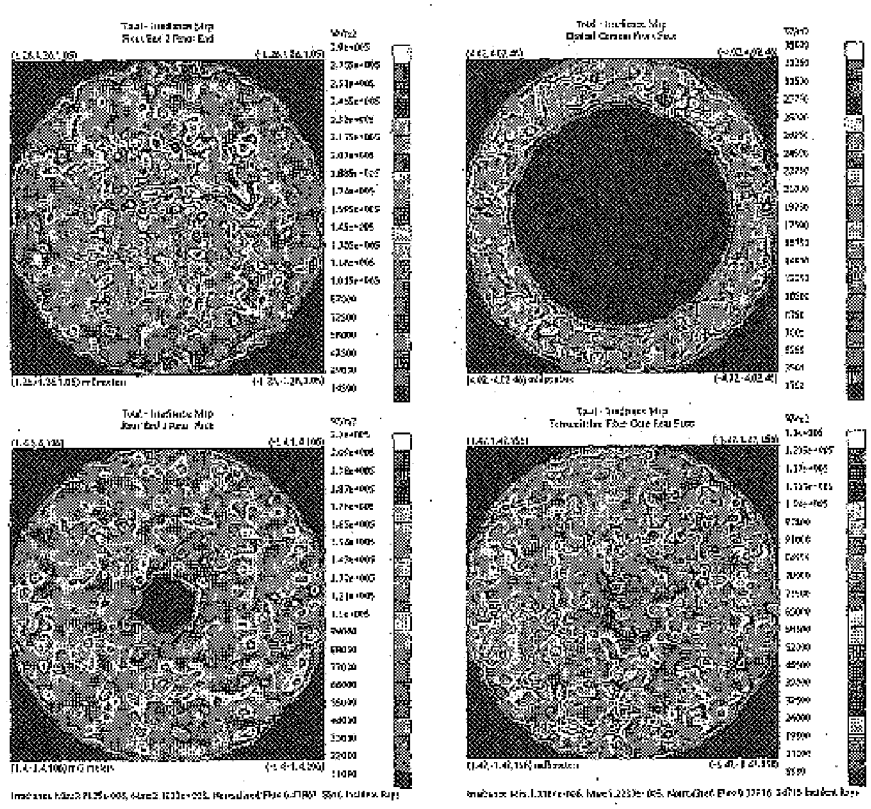

FIG. 12 collectively illustrate an intensity distribution at various cross-sections of (f2-r1).

Figure 13A:
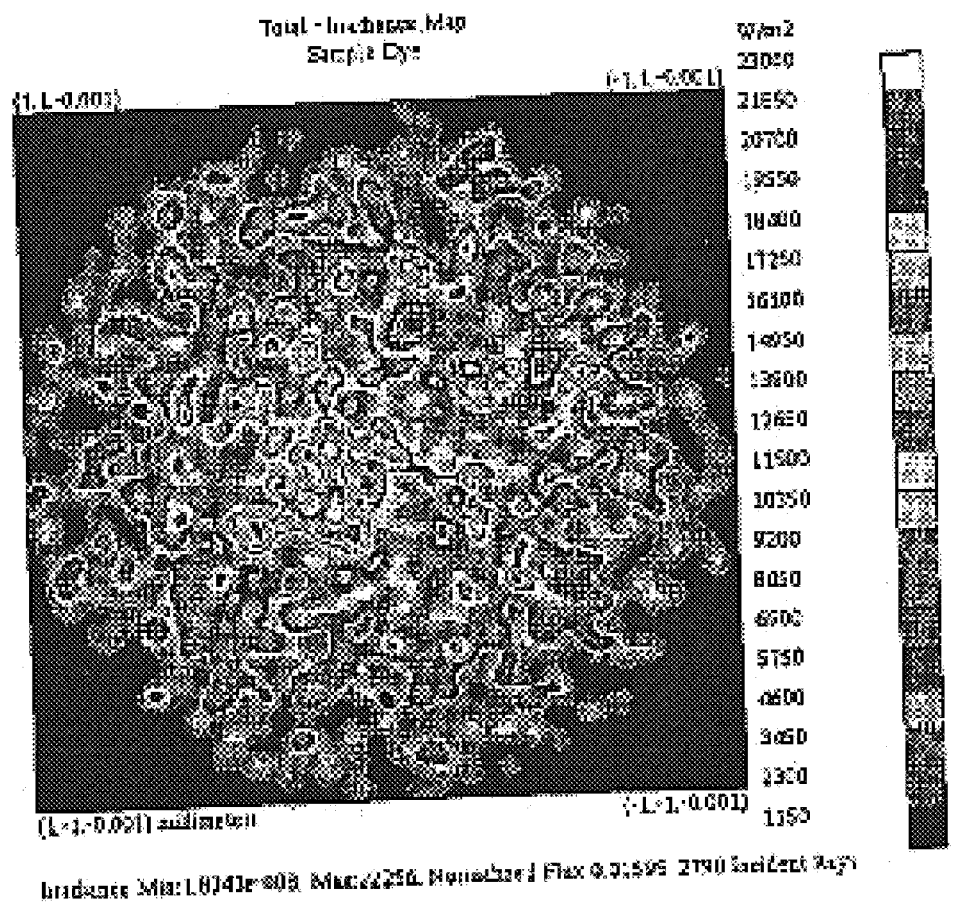
Figure 13B:
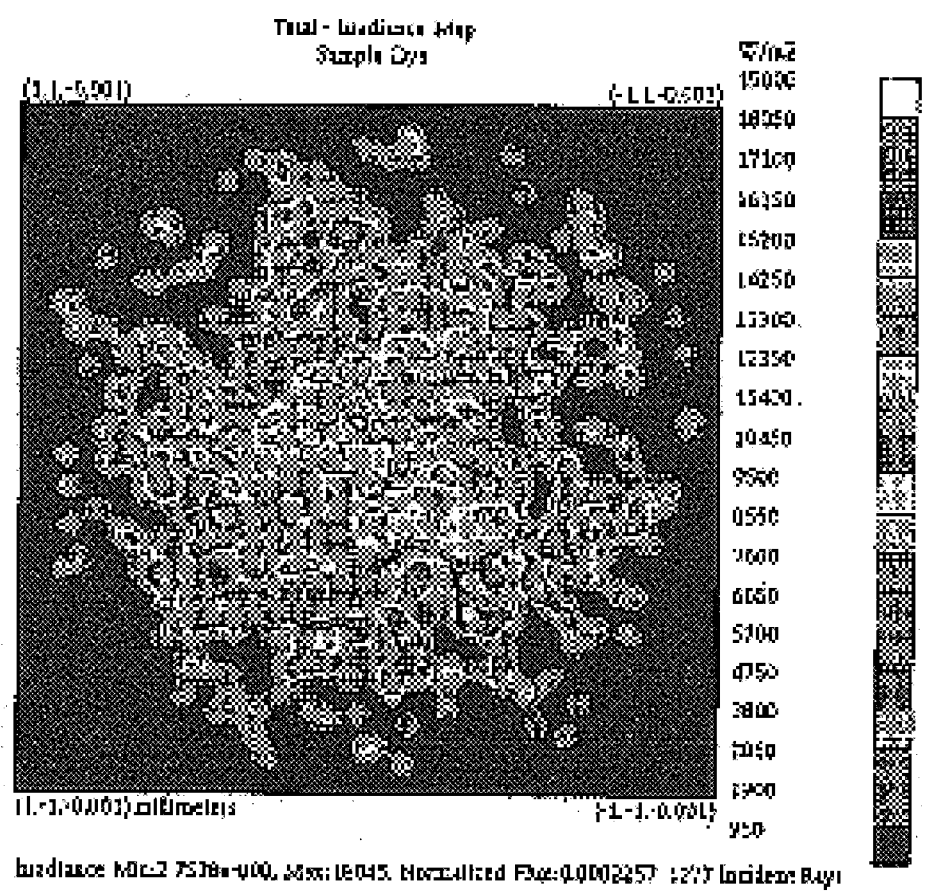

FIG. 13 illustrates the irradiance pattern at sample area by light from detector; (a) f1-r2, (b) f2-r1.

DESCRIPTION OF THE PREFERRED EMBODIMENT(S)

Figure 1:
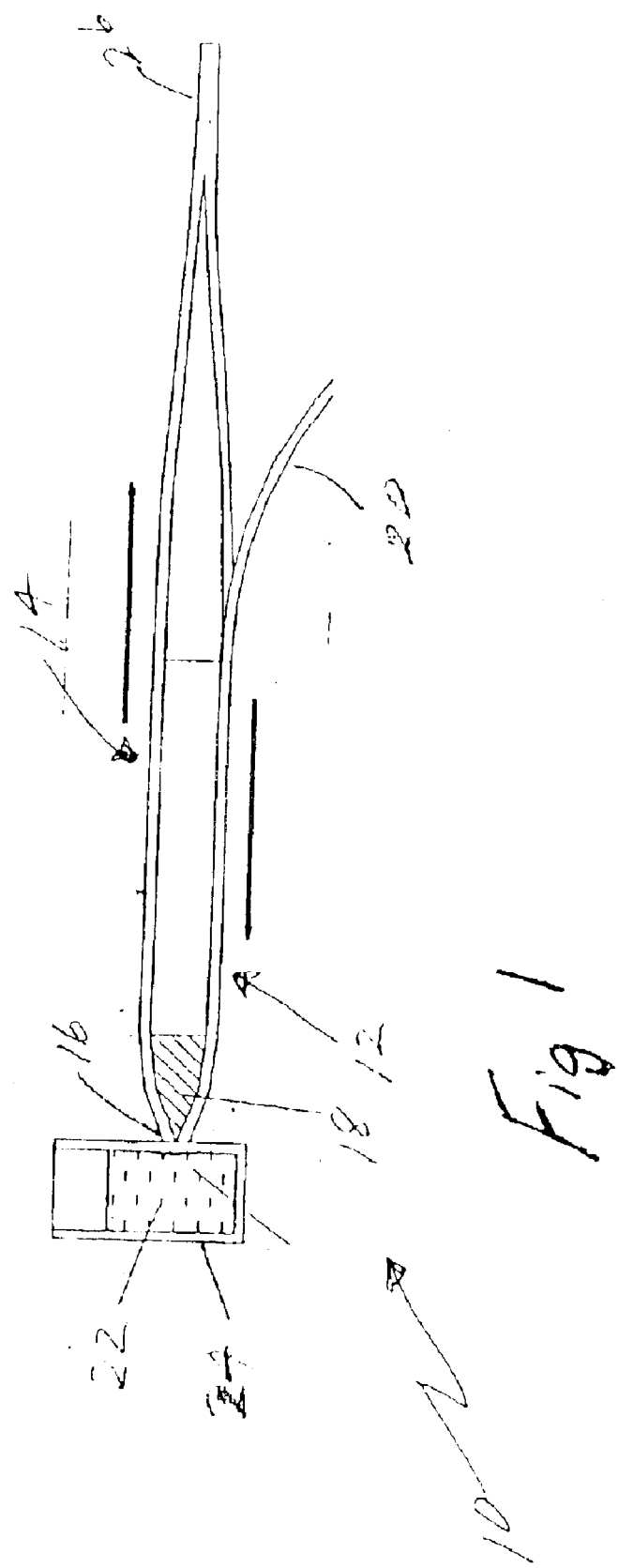
FIG. 1 is a schematic of the waveguide probe embodying the invention.

Referring to FIG. 1, a hollow optical waveguide probe 10 is shown having a first tube 12 and a second tube 14 having substantially the same dimensions. The tubes 12 and 14 converge to zero degrees and form a proximal end 16. A magnet 18 is positioned in the proximal end 16. An excitation fiber 20 is in communication with the first tube 12.

A sample 22 containing the antigen/antibody/fluorescent antibody complexes is contained in a cuvette 24 and the cuvette 24 is positioned in front of the proximal end. The proximal end 16 is polished to form a glass receiving aperture which in diameter is approximately 2 times the wall thickness of the tube 12, e.g. 2 mm in diameter. This is significantly larger than prior art optical fibers used as probes. Excitation light is injected into the excitation fiber 20, which excitation fiber is preferably attached to the middle of the first tube 12. The magnet 18 attracts the complexes 22 to the wall of the cuvette 24. The light illuminates the inner surface of the wall and the complexes 22, and the resulting fluorescent signal is guided through the second tube 14 to a distal end 26 where the tubes 12 and 14 converge.

Figure 2:
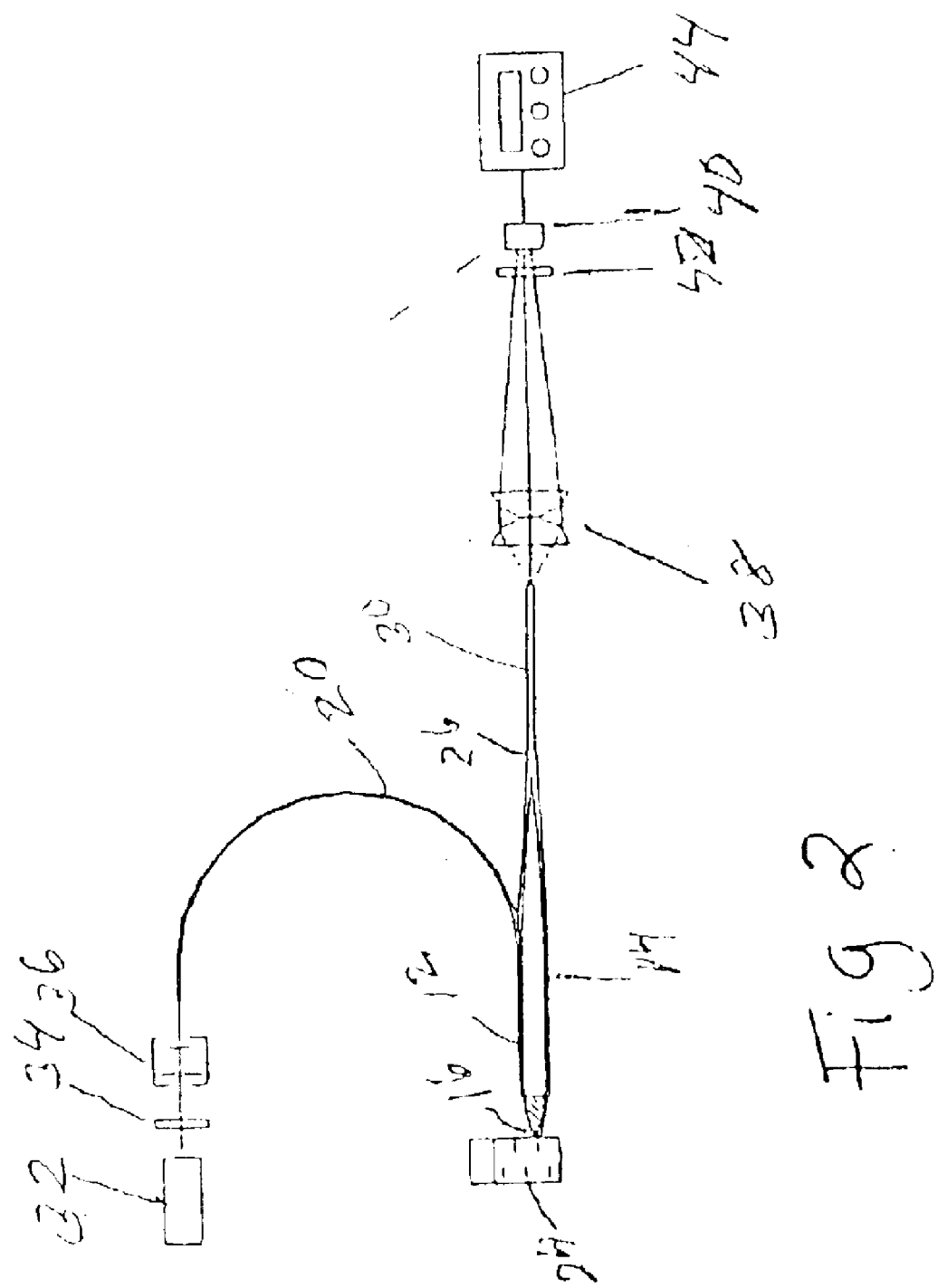
FIG. 2 is schematic of the waveguide probe embodying the invention in an optical setup.

Referring to FIG. 2. the fluorescent signal is transmitted to a transmission fiber 30. The proximal end 16 of the waveguide probe 10 functions as an optical probe while the distal end 26 of the waveguide probe 10 functions as the connector to the transmission fiber 30. The body of the waveguide probe 10 also functions to serve as a holder for the magnet, a directional coupler for the excitation signal and a high split-ratio coupler for the fluorescent signal.

In the preferred embodiment of the invention, the first and second tubes 12, 14 are made from borosilicate glass (ChemGlass). A rare earth cylindrical magnet (Neodymium 27 cylindrical plug magnet, 4200 Gauss, Herbach and Redman Company) is ground into the desired size and tapered shape to ensure that at least one point of the magnet 16 contacts at least a portion of the probe 10. The excitation fiber 20 is a 500-micron diameter fiber. The probe 10 is exposed in air and the air around and inside the tube serves as a low-index medium. Because of the hardness and slight irregularity of the magnet 18, it contacts the probe at only a few points, allowing the air gap to serve as the low-index layer in this region as well. Both the proximal and distal ends of the waveguide probe taper gradually to avoid microbend losses. The proximal end portion, however, must be compatible with the magnet, which is configured to attract the paramagnetic microspheres.

The waveguide probe 10 of the invention is used in an optical setup for detecting 670-nm emission from Cy5 dye, using a 635-nm, 3-mW laser diode, 32, (PPMT03, Power Technology) as the exciting light source. The excitation efficiency at 635 nm is about 70% of the peak value at 650 nm. The laser beam passes through a 635-nm line filter (635DF10, Omega Optical) 34 and is focused into the core of the excitation fiber 20 by collimator 36. At the end of the excitation fiber 20, exciting light is launched into the first tube 12 through the proximal end 16 and finally projects onto the inner wall of the cuvette 24. The emitted fluorescent light from the cuvette is collected by the proximal end 16, travels inside the second tuibe 14 to the distal end 26 which is in communication with the transmission fiber 30. The beam emits into free space from the transmission fiber 30. A pair of large diameter short focal-length condenser lenses 38 (25 mm effective focal length, 50 mm effective aperture) focus the image on a PIN photo detector 40 (818-SL, Newport). The front of the PIN detector is covered with a 670-nm long-pass filter 40 (670REFLP, Omega Optical) to remove reflected laser light. Because the beam entering the filter is slightly converging, the cutoff wavelength has shifted to 668 nm. The photo detector 40 is connected to a Newport (Model 835) powermeter 44. The limiting short-term stability of this system is about 1 picowatt.

EXAMPLE 1

Figure 3:
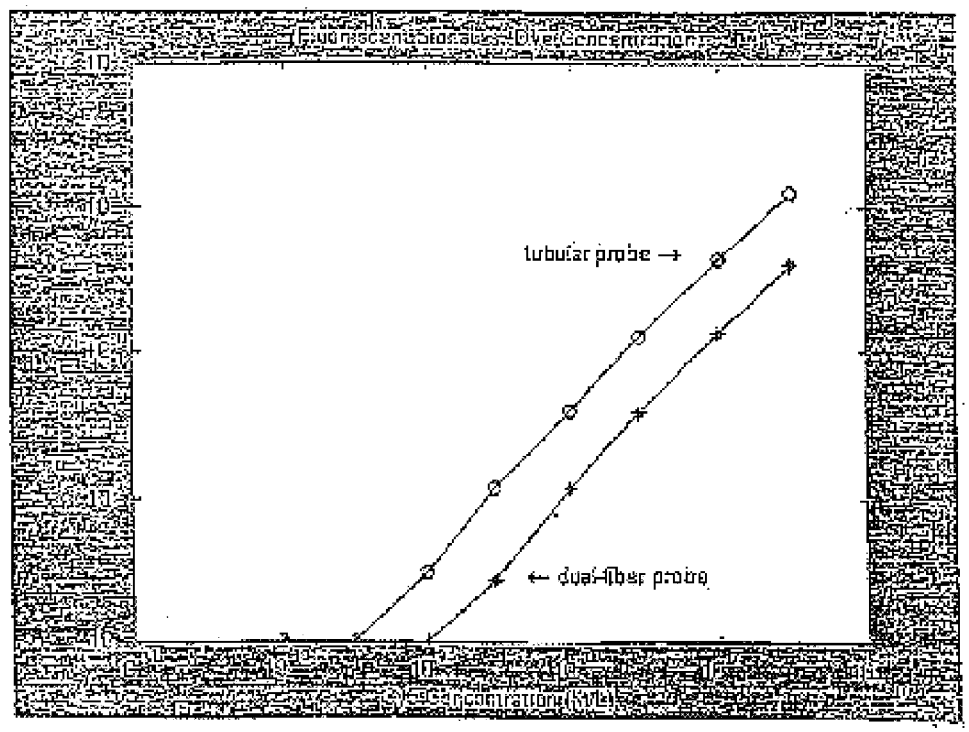
FIG. 3 is a chart depicting a comparison between the waveguide probe the dual-fiber magnetic-focusing immunosensor in testing Cy5 solutions.

Pure Cy5 dye solutions with a variety of concentrations were prepared and placed in cuvettes. The results are shown in FIG. 3, where comparison is made with the dual fiber probe disclosed in the parent application. In this test, without paramagnetic microspheres, the excitation beam illuminated the volume of the cuvette. The threshold for detection above the noise floor is seen to be at a concentration of about $2 \times 10^{-10}$ MIL for the waveguide probe, a half order of magnitude better than the dual fiber probe.

EXAMPLE 2

Figure 4:
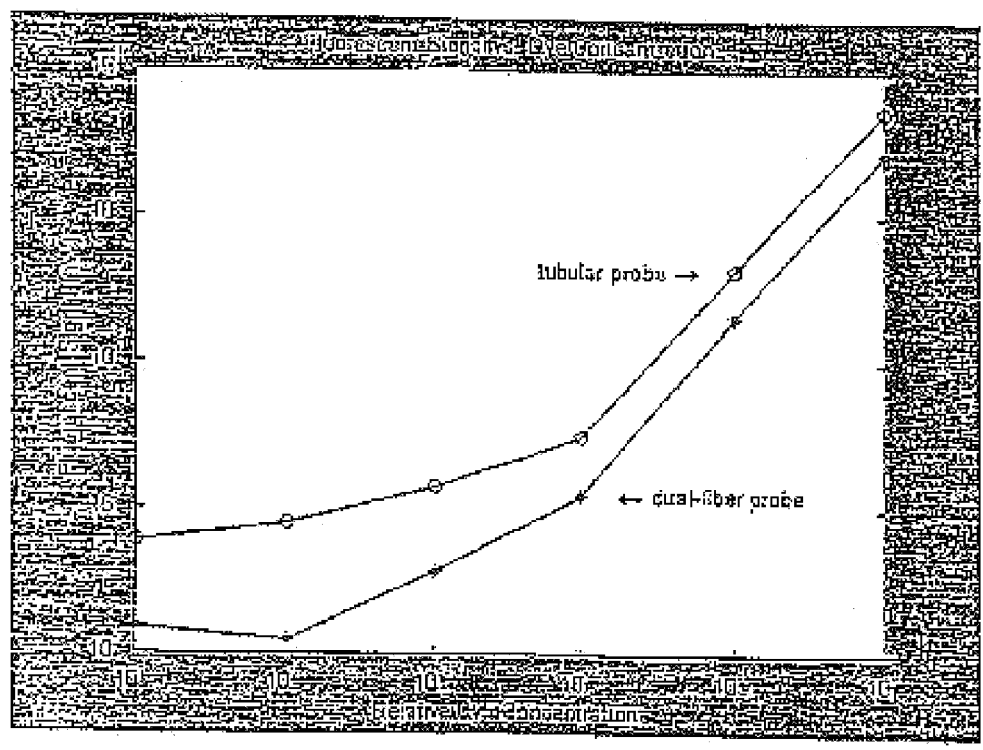
FIG. 4 is a chart depicting a comparison between the waveguide probe and the dual-fiber magnetic-focusing immunosensor in testing labeled magnetic microspheres.

A similar test was made using the 5-micron diameter, glass-beaded paramagnetic microspheres, some of which were protein-coated and labeled with Cy5 dye. The results are shown in FIG. 4. For each measurement, the total number of spheres, labeled and unlabeled, remains constant. The fraction that is labeled is referred to as the relative concentration. Again, the waveguide probe gives a signal about a half order larger than the dual fiber probe.

The waveguide probe focused paramagnetic microspheres in front of the optical probe and detected a greater signal with its improved optical aperture.

Ray Trace Analysis

In another aspect of the invention, the function of the waveguide probe is to deliver excitation light to a sample spot about 2 mm in diameter at the inside wall of a cuvette, to collect the fluorescent signal from excited Cy5 dye, and to guide it to the optical detection system. Using a non-sequential ray-trace program that incorporated Fresnel calculations of reflection and refraction at each interface (TraceProg®, Version 2.04, Lambda Research Corp. Littleton, Mass.), several waveguide probes were designed based on the following parameters: (a) uniform excitation of the dye distribution, (b) minimization of the reflected and scattered excitation light that reaches the detector, (c) a large optical aperture to the detector, and (e) an acceptable compromise between the waveguide geometry and the magnet geometry.

Model Construction

Figure 5:
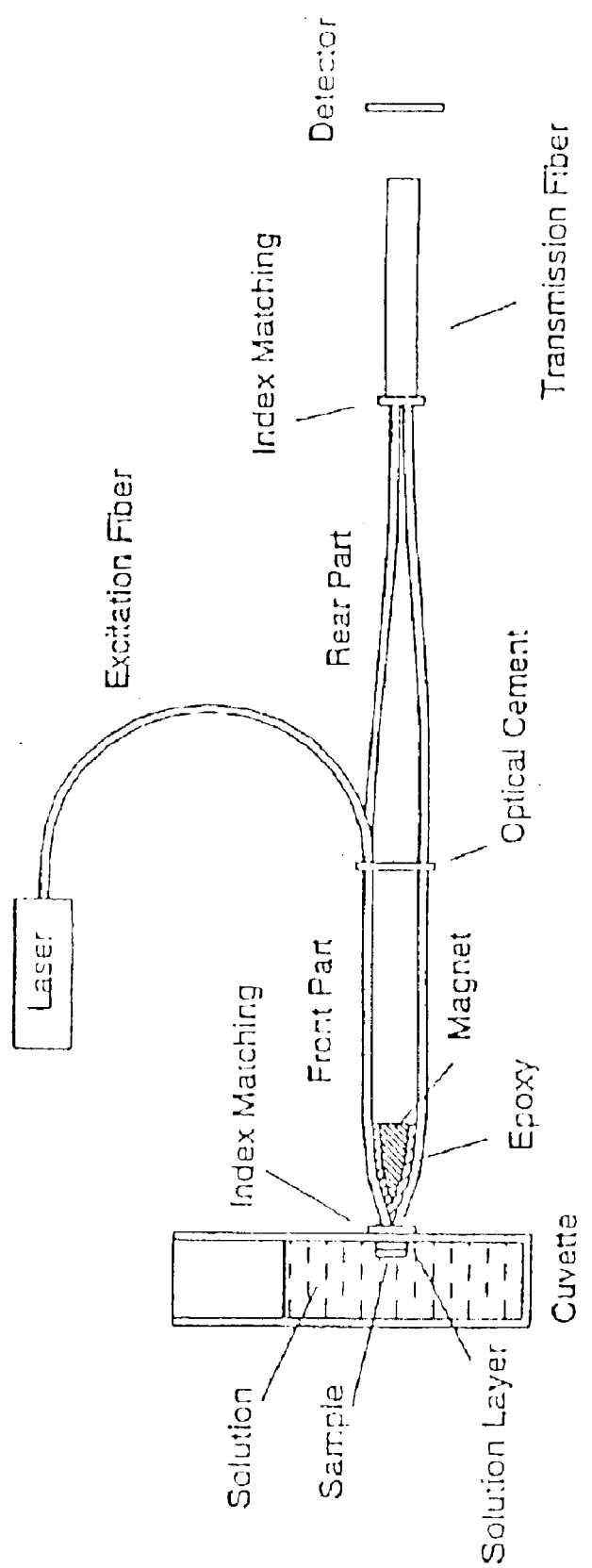
FIG. 5 is a model for numerical simulation using non-sequential raytrace (not to scale).

The model to be evaluated using the ray-trace software is illustrated in FIG. 5. The volume and/or surface properties of each element were as follows:

Laser: Disk with radius equal to that of the excitation fiber. Surface facing the fiber is set as a light source with emission normal to the surface;

Excitation fiber: Composed of a torus object and hollow torus object, originally generated separately in AutoCAD (Release 14, AutoDesk, Inc.). Core and cladding diameters are 0.486 mm and 0.500 mm, respectively, and refractive indices are 1.492 and 1.402. Attenuation is set at 0.0005/mm. The attenuation here and elsewhere in the model has little effect on the results, but shortens the calculation by tending to eliminate heavily skewed rays that would miss the detector anyway. The fiber is curved with a radius of 50 mm so that it also serves as a scrambler. Light entering the fiber parallel to the axis will be emitted with a divergence governed by the numerical aperture;

Cuvette: Has wall thickness of 1.0 mm with walls separated by 10 mm. Material property is "acrylic" with index 1.488 at 656.3 nm;

Solution: A block $10 \times 10 \times 35$ mm$^3$ with property set as "water";

Sample: This represents a layer of fluorescent dye molecules. A disk with diameter 2 mm and thickness 0.5 mm is given the volume property of "water". The surface facing the probe is either a Lambertian source for evaluating the collection efficiency of the probe or as a perfect absorber for measuring the excitation efficiency;

Solution layer: A disk of "water" with thickness 0.002 mm for simulating a water gap between the dye molecules and the cuvette wall;

Index matching (front and rear): A "water" layer 0.05 mm thick to simulate the situation in the laboratory. If no matching fluid is use, the material property is set as "air";

Magnet: A tapered cylinder. Its surface is set as a perfect absorber;

Epoxy: A layer 0.05 mm thick between the magnet and the waveguide front part. Material property set as "Epo-tek 314" with index 1.494 at 656.3 nm;

Waveguide probe, front and rear part: Material is "glass" with index 1.60 at 656.3 nm and attenuation coefficient of 0.0005 mm$^{-1}$. Dimensions will be discussed below. These waveguides are constructed in AutoCAD from a series of tapered annuli. The front parts contain, on average, 35 units and the rear parts, 80–100;

Optical cement: A disk with thickness 0.05 mm and material property set as "Epo-tek 301" with index 1.539 at 656.3 nm;

Transmission fiber: Structure and optical properties are the same as the excitation fiber. Three different dimensions were used and core/cladding diameters of 1.470/1.50, 1.958/2.00, and 2.938/3.00 mm. The length of the fiber was set at 50 mm to leave space for rays outside the fiber's numerical aperture to esacpe;

Detector: A disk of radius 5 mm located 8 mm from the end of the transmission fiber. The front surface is set as a perfect absorber.

A primary goal of this project is to predict the optimal shape of the waveguide probe so that a laboratory trial-and-error method could be abandoned. To this end, a number of different shapes, illustrated in FIG. 6, were investigated.

Ray Trace Procedures

To evaluate this type of waveguide probe system, four different types of raytrace were used.

1. The laser is the source that injects light through the excitation fiber into the front part of the waveguide parallel to the axis of the waveguide. From this is determined (a) the distribution of light on the sample disk in order to determine the efficiency of excitation of the dye molecules and (b) the amount of reflected light reaching the detector that will be background noise if not completely filtered.

2. With the laser as the source, the position of the distal end of the excitation fiber is varied to improve the light distribution on the sample disk.

3. The sample disk is a Lambertian source simulating fluorescence emission. This is used to test transmission to the detector for different shapes and sizes of the tubular waveguide probe components.

4. The detector is treated as a Lambertian source to discover the resulting irradiance distribution on the sample disk in order to predict the optimal distribution of dye molecules at the cuvette wall.

A number of software parameters were selected to achieve the best compromise between high accuracy and reasonable computation time. The chosen parameters were:

Threshold: Threshold determines how long a ray is followed. At most surfaces the ray intensity attenuates; if it reaches the threshold value, the trace is terminated. In most cases, the threshold was set as 0.01 times the initial ray intensity. For laser reflection into the detection (1.(b), above), 0.000 was used.

Number of rays: Due to the use of a Monte Carlo technique, all irradiance calculations are statistical averages depending on the random seed used. Increasing the number of starting rays will increase the consistency of the results. For initial qualitative runs, 100 rays were used. For quantitative runs, 10,000 rays were necessary to keep the variation of successive runs below 1%. Using 10,000 rays calculation 3 above, for example, took 30 minutes on a 450-MHz Pentium III computer with memory use optimized.

Results

Figure 6:
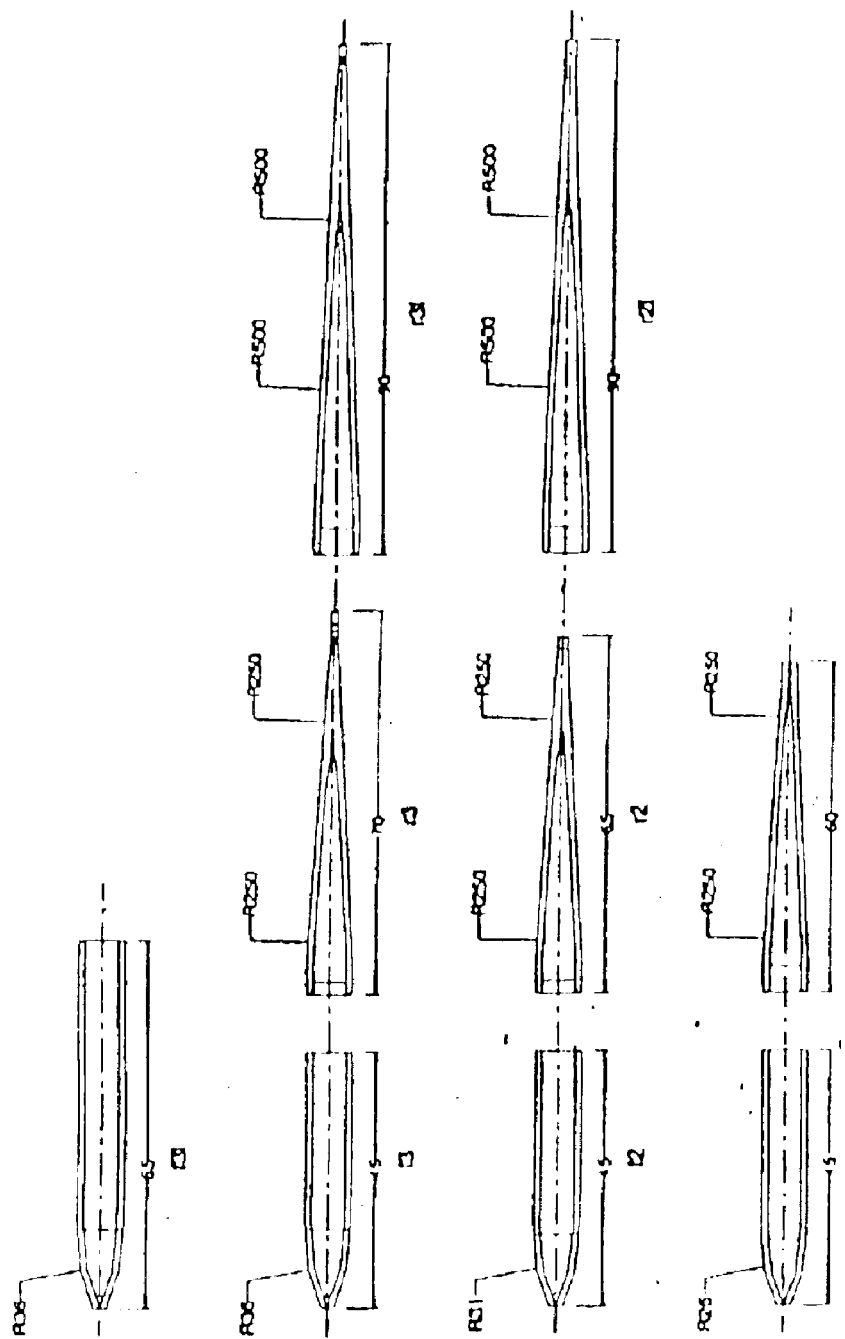
FIG. 6 illustrates components used for building waveguide probe models.
Figure 7:
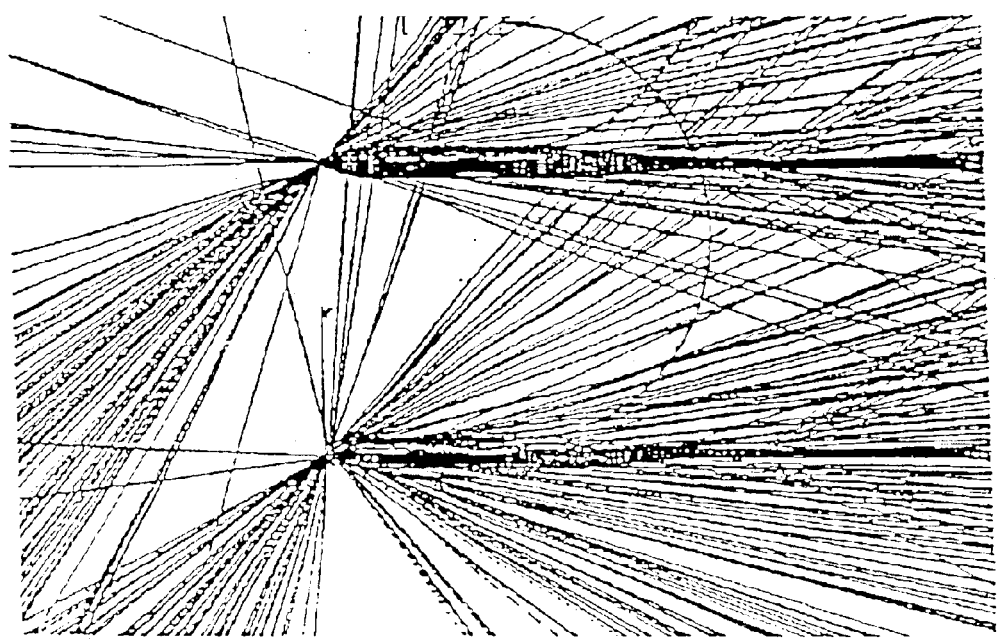
FIG. 7 illustrates a comparison of two front parts with different tapering speed.
Figure 8:
FIG. 8 illustrates a radiance pattern of a tapered tubular waveguide.

Preliminary examples of ray-trace calculations are shown in FIG. 7, where two waveguide probes with different front-end curvatures are compared. The laser is the source and light is injected into the waveguide through the excitation fiber (the semicircular loop above the waveguide) that is attached to the waveguide parallel to its axis. The rays emitted from the waveguide to the left and downward are those that would excite the fluorescent dye, but the cuvette and sample disk are absent in this example-emission is directly into the water. The highly asymmetric distribution is due to the way the excitation fiber is connected to the waveguide. Rays fanning out to the right are lost due to reflections from the flat ends of the waveguides and to the curvatures of the front ends. In the two samples shown, the top waveguide's front end has a radius of curvature of 26 mm and the bottom, 21 mm. The shorter radius appears to produce considerable more reflection losses and a smaller transmitted signal. As a result, the front-end curvatures considered in FIG. 6 begin at 26 mm. The waveguides themselves appear black because they are filled with reflected, guided rays. The calculated results are consistent with earlier observations (FIG. 8), where emission from the tip of a waveguide submerged in water was observed from the side.

Figure 9A:
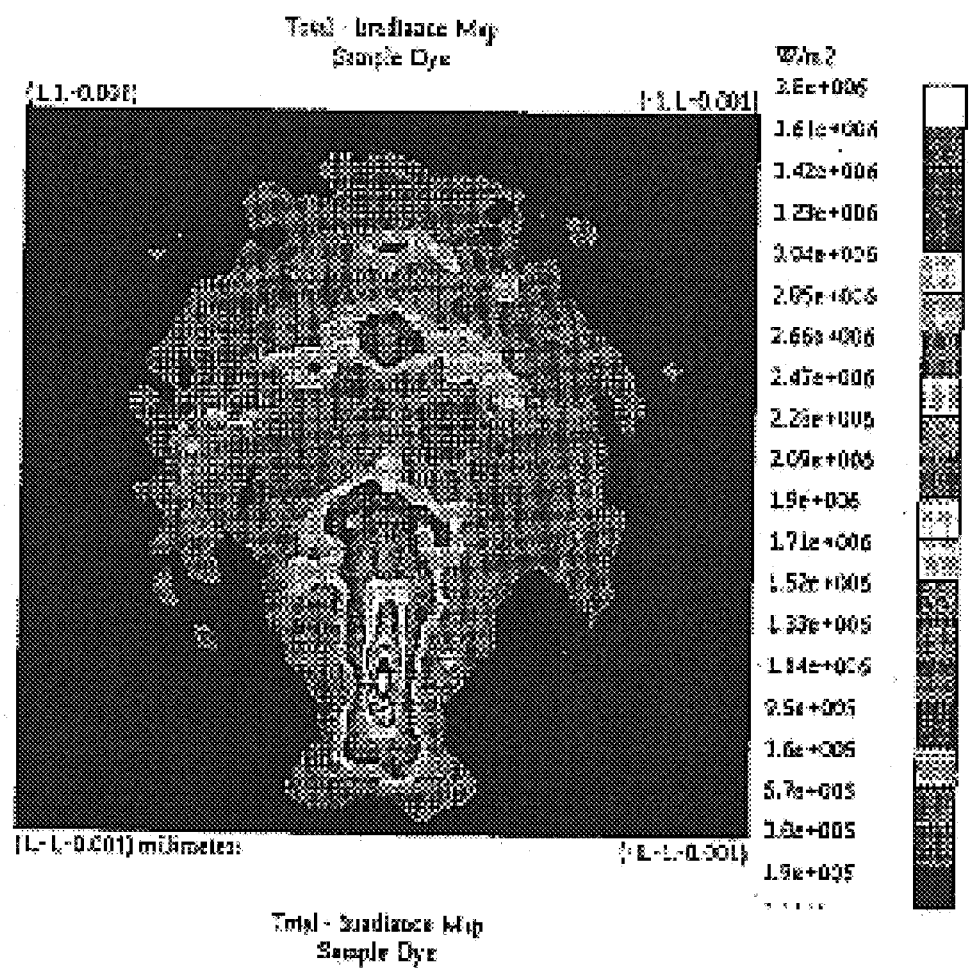
FIG. 9 illustrates the irradiance distribution at sample area by various front parts. (a) irradiance pattern by f1, normalized flux: 0.878; (b) irradiance pattern by f2, normalized flux; 0.880; (c) irradiance pattern by f3, normalized flux: 0.882; (d) by f31, normalized flux: 0.872.
Figure 9:
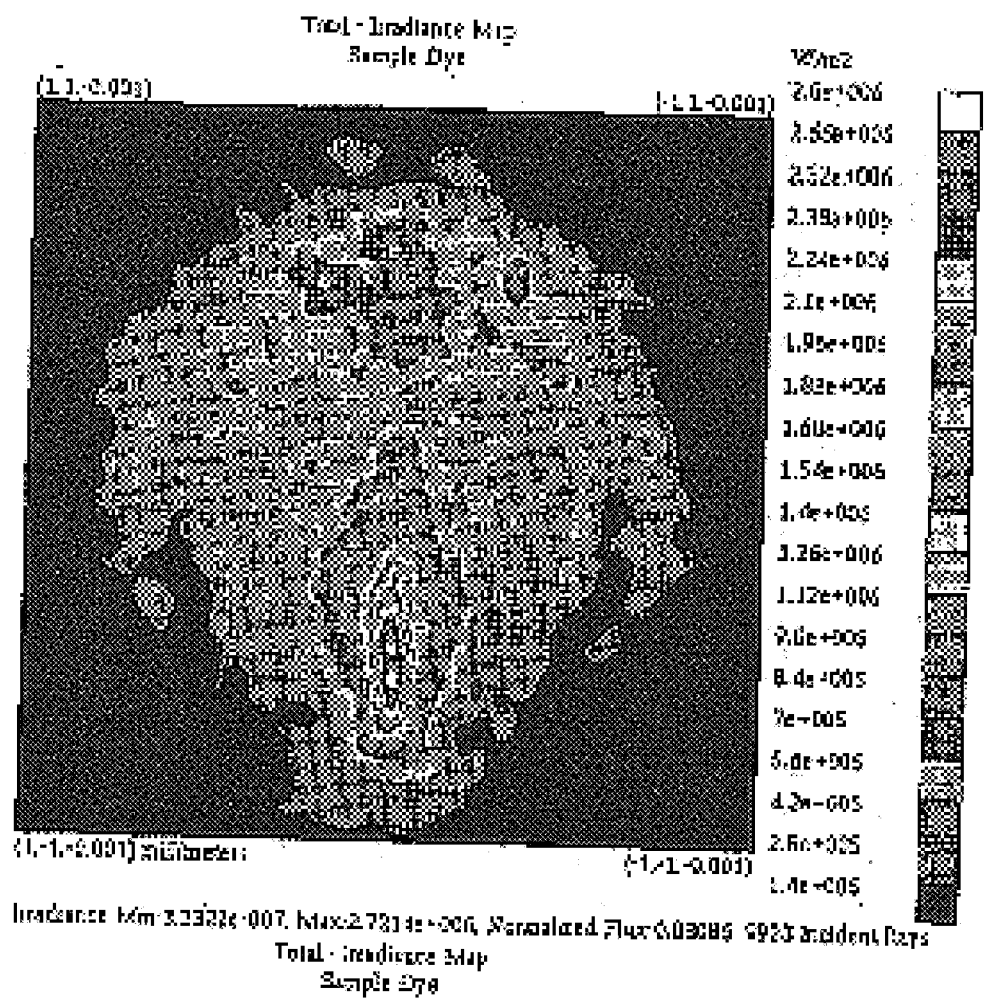
Figure 9C:
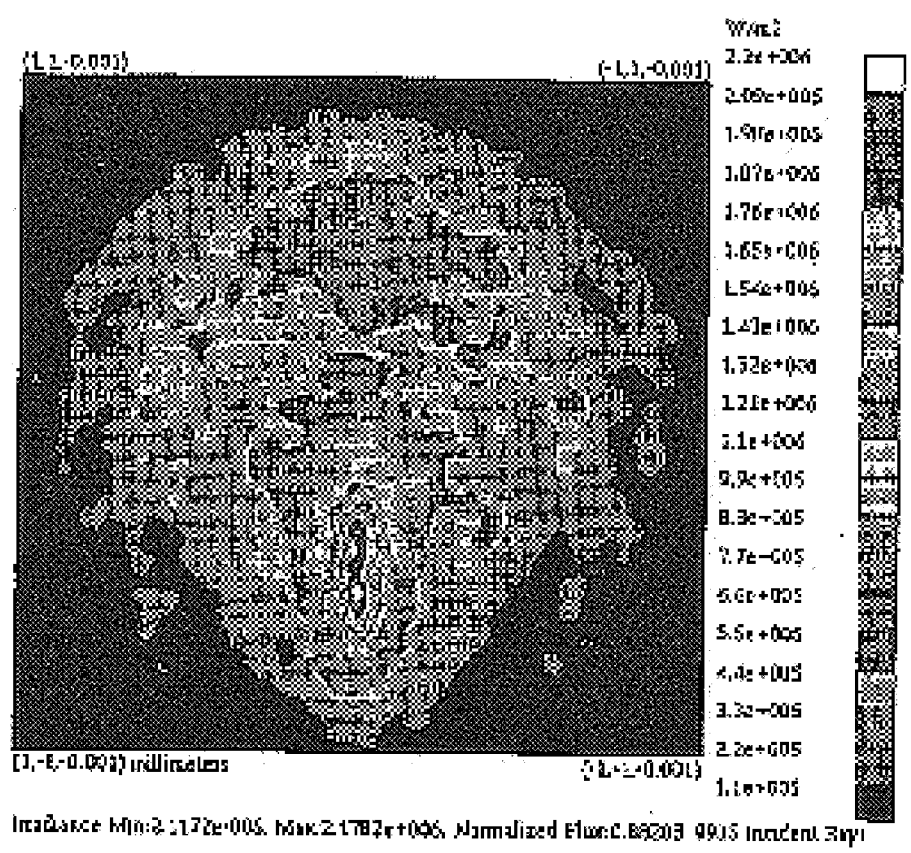
Figure 9:
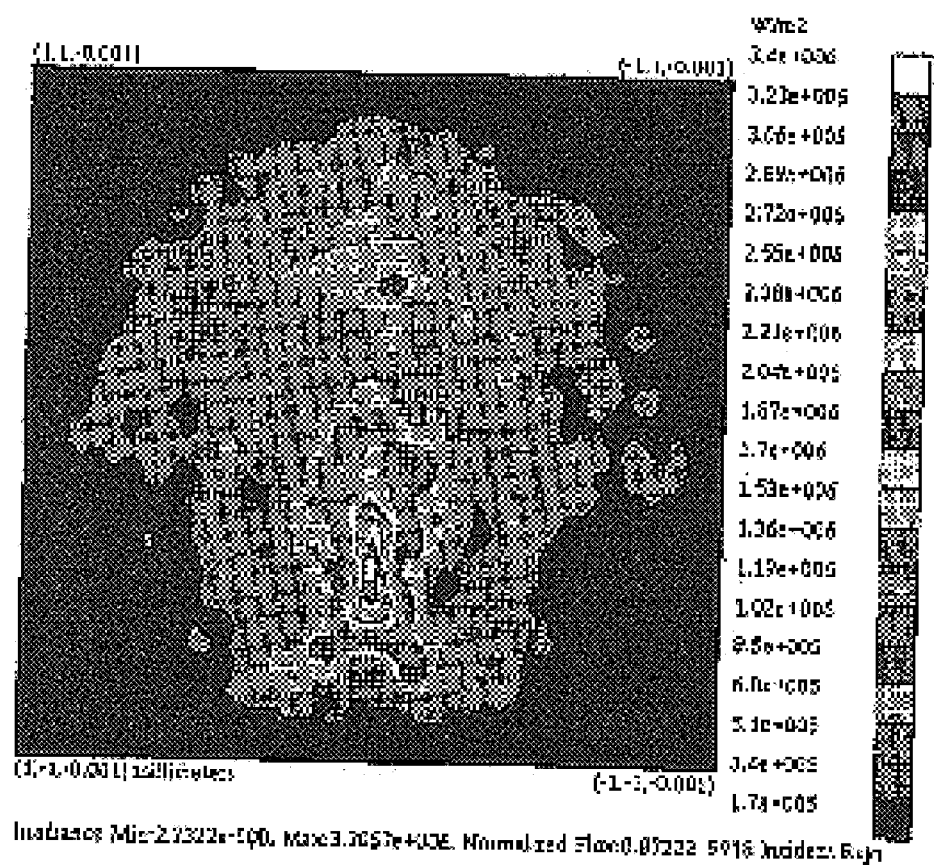

Laser Light Injected into the Waveguide Probe with Excitation Fiber Parallel to the Axis To test the excitation frequency of the four waveguide front ends shown in FIG. 6, light was first injected into the waveguide probe with the excitation fiber parallel to the system axis. Irradiance maps at the sample front surface (i.e. at the dye distribution) are shown in FIG. 9.

It is observed that the radius of curvature of the front end has only a small effect on the irradiance pattern at the sample. They are all highly localized and asymmetric and have total irradiance between 87% and 88% of the laser signal.

Some of the laser light is reflected by the cuvette walls and the front end of the waveguide, is guided back to the detector, and will raise the minimum detection level if not completely filtered. This was simulated by making the sample completely absorbing (although in real life significant scattering occurs here). For waveguide components (See FIG. 6) f1-r1, f2-r2, and f3-r1, the signal at the detector falls between 0.26% and 0.29% of the laser signal. These results are summarized in the first three rows of table 1.

TABLE 1

| | Excitation Efficiency | Background Noise |
|---|---|---|
| f1-r1 | 0.88 | 0.0027 |
| f2-r2 | 0.88 | 0.0026 |
| f3-r1 | 0.88 | 0.0029 |
| f2-r2 | 0.88 | 0.0017 |
| f2-r21 | 0.88 | 0.0017 |
| f2-r3 | 0.88 | 0.0012 |
| f2-r31 | 0.88 | 0.0011 |
| f31-r1 | 0.87 | 0.0028 |
| f2-r1, 50 dgr | 0.87 | 0.0011 |
| f2-r1, 55 dgr | 0.80 | 0.00020 |
| f2-r1, 60 dgr | 0.52 | $6.93 \times 10^{-6}$ |

Varying the Location of the Distal End of the Fiber

Figure 10A:
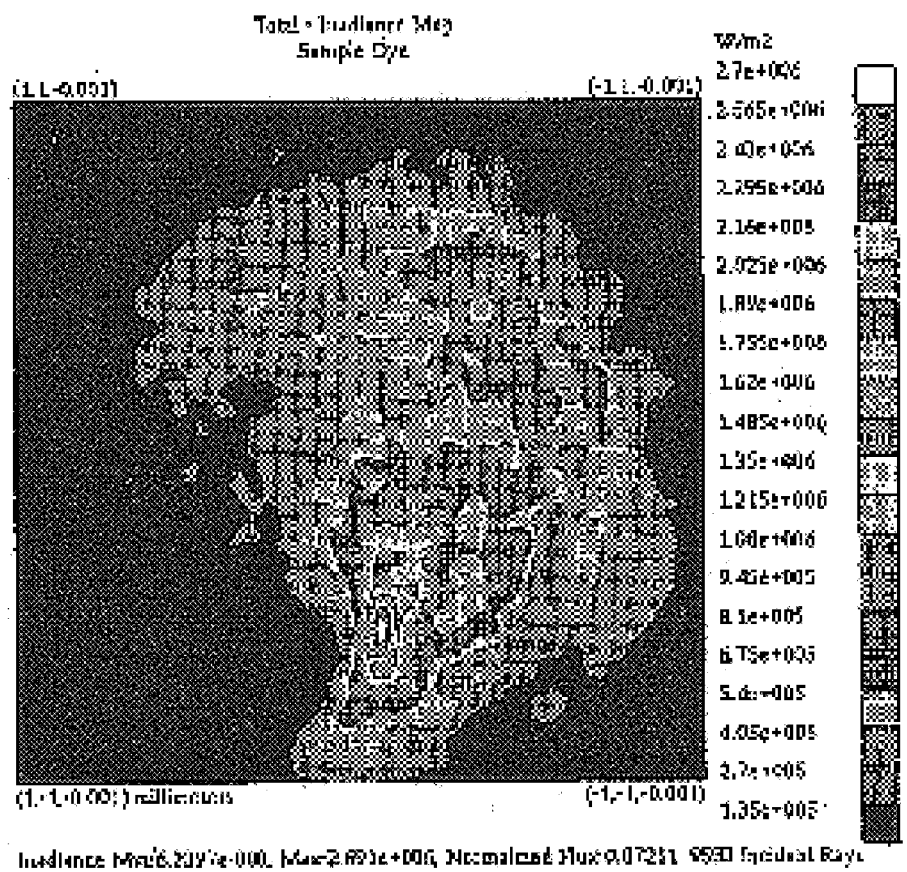
FIG. 10 illustrates irradiance maps with the excitation fiber at a tilted angle: (a) 2 degrees; (b) four degrees.
Figure 10B:
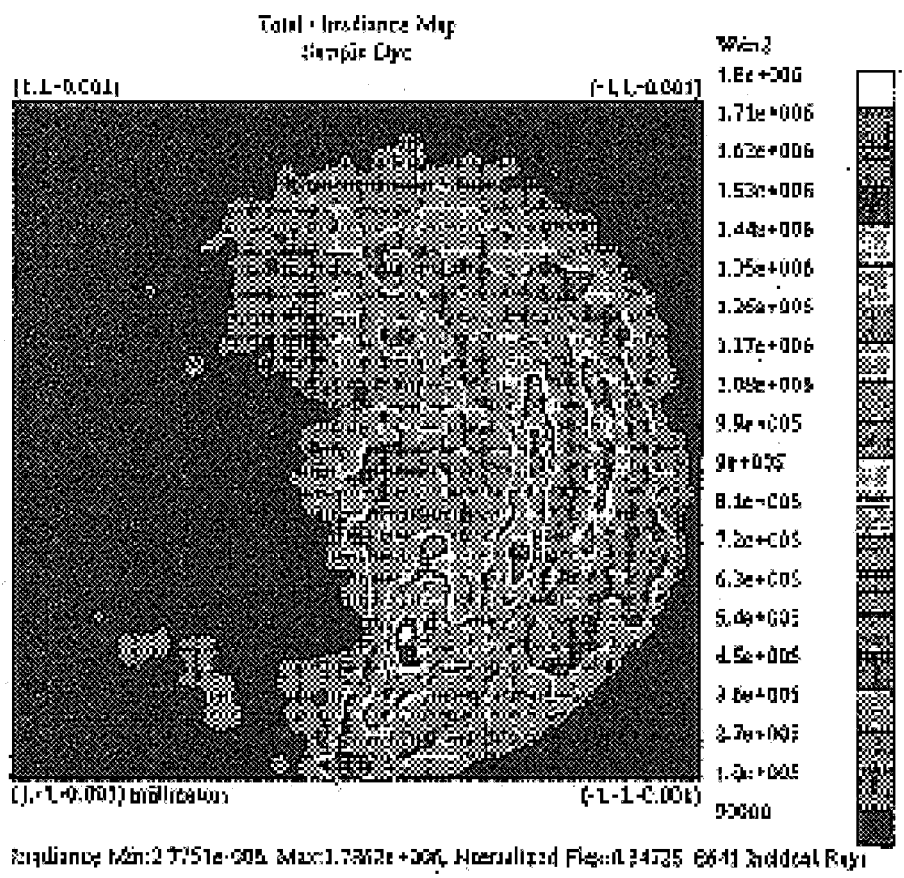

A simulation was used to see if small changes in the location of the fiber could improve the distribution of the exciting light. FIG. 10 shows the results when the tip of the excitation fiber is rotated two degrees and four degrees laterally away from the axis of the waveguide probe. At two degrees, there is not much change in the peak of the distribution. At four degrees, the pattern is becoming more uniformly distributed, but is still drastically asymmetric and the irradiance has reduced slightly to 85%.

Figure 11:
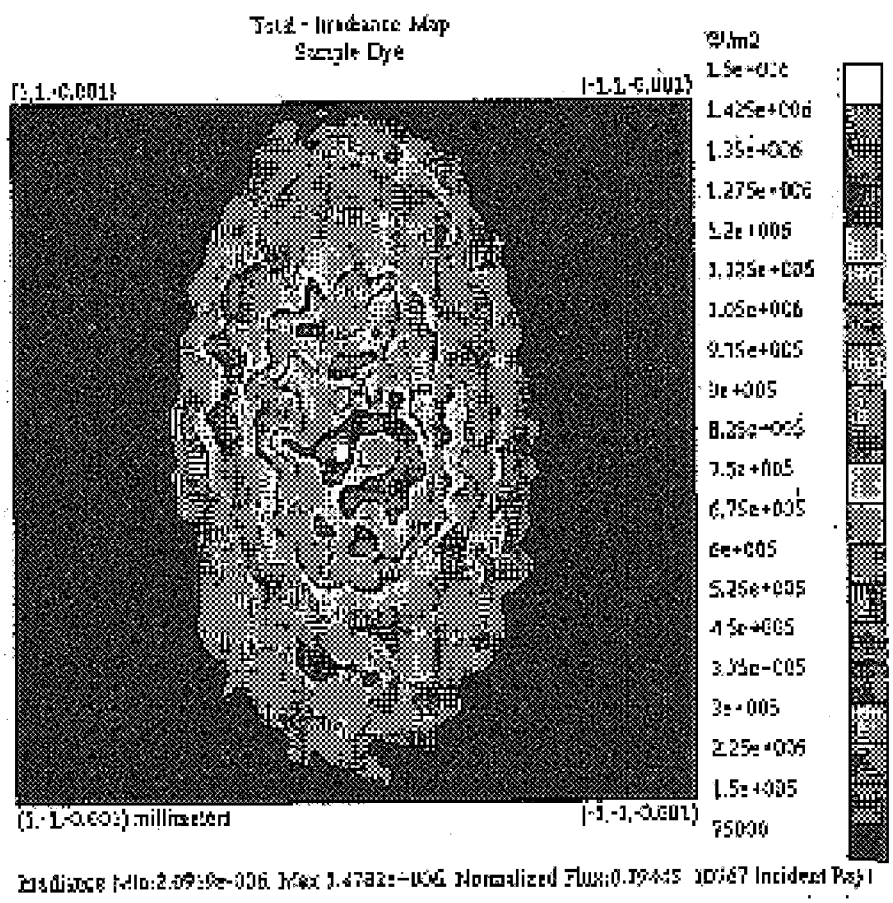
FIG. 11 illustrates a sample-disk irradiance with fiber at the cuvette wall.

A model was developed with the tip of the excitation fiber against the cuvette wall adjacent to the waveguide, tilted at an angle θ from the waveguide axis. The irradiance pattern at the sample disk for θ=55° is shown in FIG. 11. The pattern is centered on the disk and is reasonably uniform. The price is a reduction in total irradiance to 79% of the laser signal. The results for 50°, 55° and 60° are shown at the bottom of table 1. The irradiance at the sample disk changes rapidly with angle (63° is the critical angle for total internal reflection at the cuvette-water interface) as does the reflected laser light reaching the detector, which is reduced to 0.02% at θ=55° and to a negligible level (compared to presumed scattering levels) at 60°.

Transmission from the Fluorescent Source (Sample Disk) to the Detector

The laser source is turned off and the 2-mm diameter sample disk is made a Lambertian source with a flux of 1 W/m$^2$ and with 10,000 starting rays. The complete run for the waveguide combination f2-r1 is shown in FIG. 12. FIG. 12(a) shows that about 60% of the Lambertian emission reaches the front face of the waveguide. On this run, each measured surface was made a perfect absorber to eliminate rays reflected from following surfaces, which would be included by the software in the irradiance calculation). Curvature losses in the front end reduce the irradiance at the f2-r1 interface to 50% of the source (FIG. 12(b)). The cross-sectional scales in FIG. 12 are not consistent. FIG. 12(a) shows the interface between the rear end segment and the transmission fiber, where the irradiance has only reduced to 48%. The mismatch of the numerical apertures of the rear end and of the transmission fiber, however, reduce the signal at the far end of the fiber to 38% (FIG. 12(d)). Finally, divergence from the end of the fiber, especially of skew rays, results in 23% of the source signal reaching the detector in this model.

A summary of results for the collection and transmission of the Lambertian signal for all of the f*-r* combinations of the waveguide is given in table 2. It is noted that front ends with radii of curvature between 26 mm and 36 mm behave identically (first two columns). For the rear ends, there is no distinction between radii curvature of 250 mm and 500 mm. Those named r3 and r31, which taper to a smaller final diameter, undergo somewhat greater losses than the others (third column). The greatest distinction occurs at the coupling from the rear end (r3) to the transmission fiber. A smaller final diameter of the waveguide rear end results in greater loss at the far end of the fiber (fourth column). The loss here is due presumably, to the mismatch of numerical apertures. Finally, spread from the end of the fiber determines the signal at the detector.

TABLE 2

Irradiance at various cross-sections for waveguides f*-r*

| | Collecting Efficiency (at front) | Collecting Efficiency (at cement) | Collecting Efficiency (at optical matching) | Irradiance at the End of Fiber | Signal Detected (at PIN) |
|---|---|---|---|---|---|
| f1-r1 | 0.62 | 0.51 | 0.49 | 0.39 | 0.23 |
| f1-r1 | 0.62 | 0.51 | | | 0.12 |
| f1-r1 | 0.62 | 0.51 | | | 0.061 |
| f1-r1 | 0.60 | 0.50 | 0.48 | 0.38 | 0.23 |
| f1-r1 | 0.60 | 0.50 | 0.47 | 0.30 | 0.12 |
| f1-r1 | 0.60 | 0.50 | 0.46 | 0.30 | 0.11 |
| f1-r1 | 0.60 | 0.50 | 0.37 | 0.19 | 0.061 |
| f1-r1 | 0.60 | 0.50 | 0.37 | 0.19 | 0.058 |
| f1-r1 | 0.59 | 0.49 | 0.47 | 0.37 | 0.23 |
| f1-r1 | 0.59 | 0.49 | | | 0.12 |
| f1-r1 | 0.59 | 0.49 | | | 0.12 |
| f1-r1 | 0.59 | 0.49 | | | 0.063 |
| f1-r1 | 0.59 | 0.49 | | | 0.061 |
| f1-r1 | 0.59 | 0.49 | 0.46 | 0.37 | 0.23 |

Optimal Fluorescent Dye Distribution

The dye molecules assembled at the cuvette wall by the magnet will not likely behave as a uniformly distributed Lambertian source. This can be inferred from a simulation in which the detector is set as a Lambertian source and the rays are followed backward through the waveguide probe system to the sample disk. The result is shown in FIG. 13 for two different waveguide probe configurations. In these cases 100,000 rays were traced, because only a small fraction enter the waveguide probe due to the location and size of the detector. It can be seen that there is a somewhat higher density of rays in the center and that the central rays retain a higher intensity; i.e. they have suffered less loss in transition.

Dual Fiber Probe

A final simulation test was made to compare the tubular waveguide to the dual fiber probe disclosed in the parent application. The excitation fiber is aligned beside the magnet at an angle of 18° from the magnet axis while the tubular waveguide is replaced by a 500 μm fiber, also at 18°. The results are shown in table 3. With the laser as the light source, 95% reaches the sample and, because of the fiber separation and the small aperture of the receiving fiber, only 0.15% is reflected back to the detector as noise. The fluorescence collecting efficiency is correspondingly reduced, however. With the 2-mm diameter sample disk as a Lambertian source, less than 1% reaches the detector. The efficiency of the dual-fiber probe can be improved if the paramagnetic particles can be focused to a smaller spot. With a 1-mm Lambertian source, the fraction reaching the detector increases to 2.8%.

TABLE 3

Simulation Result of the Dual Fiber Probe

| | Excitation Efficiency | Background Noise | Flux at Fiber Tip | Flux at Distal End of Fiber | Signal Detected (at PIN) |
|---|---|---|---|---|---|
| Dual fiber, 2-mm source | 0.95 | 0.0015 | 0.038 | 0.013 | 0.0089 |
| Dual Fiber, 1-mm source | 0.95 | 0.0015 | 0.048 | | 0.028 |

Discussion and Conclusions

A tapered tubular optical waveguide probe designed for use in a magnetic focusing fluorescence biosensor was simulated and analyzed with Trace-Pro, a non-sequential raytrace program from Lambda Research. The objective is to enhance the fluorescence collection efficiency and the signal-to-noise ratio in a system that incorporates a small permanent magnet. The rate of curvature of the front end of the waveguide probe was found to be relatively unimportant. This means that it can be molded to fit the shape of the tapered magnet that forms the best distribution of collected microspheres in front the waveguide. The radii of curvature of the rear part are not very important, but it is important to terminate the curvature before the outer diameter becomes too small. Injection into a large-diameter (3-mm) transmission fiber gave the best results.

Three different configurations were considered. First was the tubular waveguide probe with the laser excitation signal inserted through the front part of the waveguide probe. Secondly, the same tubular waveguide probe was separated from the excitation fiber. Finally, a dual-fiber probe was used a reference. A normalized background (NB) is defined as the ratio of laser noise at the detector to the laser excitation efficiency and a S/N ratio is taken as the efficiency of the waveguide probe in transmitting the sample-generated signal to the detector divided by NB. When normalized by the value of the dual-fiber case, the two tubular configurations have S/N of 4.4 and 52, respectively.

Not all sources of noise have been included. It is known from experiment that the accumulated paramagnetic microspheres scatter a significant amount of light, but the sample disk for the noise simulations made a perfect absorber. Since this affects all three systems, inclusion should not change the normalized S/N values significantly. Also not included in the simulations were scratches, bubbles, or other imperfections in the glass and plastic components. These are more likely to occur in the more complicated tubular waveguide probe systems and may reduce their normalized S/N's.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described our invention, what we now claim is:

1. A method for the detection of pathogens in a sample, the sample contained in a housing, comprising:

placing paramagnetic microspheres with immobilizing primary antibodies that bind with the pathogens in the housing;

placing optical markers bound to secondary antibodies that bind with the pathogens in the housing;

forming in the sample molecular complexes, each molecular complex comprising one of the pathogens bound to at least one of the primary antibodies and at least one of the secondary antibodies;

focusing the molecular complexes in a field of view of a proximal end of a waveguide probe, the proximal end comprised of a first tube and a second tube and shaped to form a receiving aperture, the aperture having a magnet received therein;

transmitting light through the proximal end and into the housing to generate a fluorescent signal from the molecular complexes;

collecting the fluorescent signal; and detecting the fluorescent signal which corresponds to the presence of the pathogens in the sample.

2. The method claim 1 wherein the antibodies are anti-*Salmonella*.

3. The method of claim 1 wherein the pathogen is *S.typhimurium*.

4. The method of claim 1 wherein the sample is selected from the group consisting of mammals, fish and fowl.

5. The method of claim 1 wherein transmitting light through the proximal end comprises:

injecting a laser beam into and through the first tube and through the proximal end.

6. The method of claim 1 wherein the housing is a cuvette.

7. The method of claim 1 wherein the first tube has a wall and the length of the diameter of the proximal end is about twice the magnitude of the wall thickness of the first tube.

8. A method for the detection of pathogens in a sample, the sample contained in a housing, comprising:

placing paramagnetic microspheres with immobilizing primary antibodies that are capable of binding with the pathogens in the housing;

placing optical markers bound to secondary antibodies that are capable of binding with the pathogens in the housing;

forming in the sample molecular complexes, each molecular complex comprising one of the pathogens bound to at least one of the primary antibodies and at least one of the secondary antibodies;

focusing the molecular complexes in a field of view of a proximal end of a waveguide probe, the proximal end comprised of a first tube and a second tube and shaped to form a receiving aperture, the aperture having a magnet received therein;

communicating an excitation fiber with the first tube;

transmitting light through the excitation fiber, first tube and into the housing to generate a fluorescent signal from the molecular complexes;

collecting the fluorescent signal; and detecting the fluorescent signal.

* * * * *